United States Patent [19]

Butow et al.

[11] Patent Number: 5,310,664

[45] Date of Patent: May 10, 1994

[54] SITE SPECIFIC DOUBLE STRANDED DNA ENDONUCLEASE

[75] Inventors: Ronald A. Butow, Dallas, Tex.; Philip S. Perlman, Worthington, Ohio

[73] Assignee: Board of Regents, The University of Texas System, Austin, Tex.

[21] Appl. No.: 997,653

[22] Filed: Dec. 28, 1992

Related U.S. Application Data

[63] Continuation of Ser. No. 456,100, Dec. 22, 1989, abandoned.

[51] Int. Cl.$^5$ .......................... C12P 19/34; C12N 9/22
[52] U.S. Cl. .................................. 435/91.53; 435/199
[58] Field of Search .......................... 435/199, 91, 942

[56] References Cited

U.S. PATENT DOCUMENTS

| | | | |
|---|---|---|---|
| 4,746,609 | 5/1988 | Bolton et al. | 435/91 |
| 4,863,858 | 9/1989 | Grosskopf et al. | 435/91 |
| 4,935,367 | 6/1990 | Leonard et al. | 435/199 |

OTHER PUBLICATIONS

Bonitz, S. G., et al. (1980) J. Biol. Chem. 255, 11927–11941.
Dujon, B. (1980) Cell 20, 185–197.
Sarguell, B. et al., (1990) Nuc. Acids Res. 18(19) 5659–5665.
Colleaux, L., et al. (1986) Cell 44, 521–533.
Wernette, C. M. (1990) J. Biol. Chem. 265 (31), 18976–18982.
Hanson et al., "Evidence for Translated Intervening Sequences in the Mitochondrial Genome of Saccharomyces cerevisiae," J. of Biol. Chem., 257(6): 3218–3224, Mar. 25, 1982.
Miklos de Zamaroczy and Bernardi, "the Primary Structure of the Mitochondrial Genome of Saccharonmces cerevisiae-a Review," Gene, 47:155–177 (1986).
Delahodde et al., "Site-Specific DNA Endonuclease and RNA Maturase Activities of Two Homologous Intron-Encoded Proteins from Yeast Mitochondria," Cell, 56:431–441 (Feb. 1989).
Wenzlau et al., "A Latent Intron-Encoded Maturase is Also an Endonuclease Needed for Intron Mobility," Cell, 56:421–430 (Feb. 1989).
Sass, Philip Michael "Mutations in the Mosaic OXI3 Gene in the Mitochondrial Genome of the Yeast Saccharomyces cerevisiae (DNA)" vol. 45/07-B Dissertation Abst. Intel., p. 2012, Indiana Univ.
Zassenhaus, Genetic and Biochemical Characterization of Mitochondrial Mutants in the *VAR1* Region of Saccaromyces cerevisiae Dissertation, 1979, Ohio State Univ., pp. 88–90.

*Primary Examiner*—Charles L. Patterson, Jr.
*Attorney, Agent, or Firm*—Arnold, White & Durkee

[57] ABSTRACT

An endonuclease which cleaves double stranded DNA at a specific site, producing staggered ends with 4 base pair, 3' overhangs, has been isolated, purified and characterized. A method of producing sufficient quantities of the endonuclease for purification and characterization is disclosed. A method to use the endonuclease to cleave DNA, producing fragments useful for gene mapping is also disclosed.

16 Claims, 6 Drawing Sheets

SITE SPECIFIC DOUBLE STRANDED DNA ENDONUCLEASE

The Government may own certain rights in the present invention pursuant to National Institutes of Health Grant Number GM355510.

This is a continuation of co-pending application Ser. No. 07/456,100, filed on Dec. 22, 1989, now abandoned.

BACKGROUND OF THE INVENTION

1. Field of the Invention

This invention relates generally to a protein, more specifically to an endonuclease protein which has not previously been purified or characterized. This endonuclease is novel and extremely useful because it cleaves double-stranded DNA at specific, infrequent sites, for which endonucleases were not previously available. The resulting fragments are of great value for human gene mapping because the cleavage site is a sequence ordinarily encountered in genomic DNA, and because cleavage by the endonuclease produces relatively larger fragments than characteristic of those produced by many previously available endonucleases. This invention also includes methods for purifying the endonuclease and for cleaving DNA by use of the endonuclease.

2. Description of Related Art (A) Restriction Endonucleases

One of the essential tools molecular biologists use to delve deeper into the mysteries of life contained in the structure of DNA, the genetic material, is a molecular scissors called a restriction endonuclease. There are many such enzymes which are capable of cutting DNA at specific sites (see Lewin, 1987 for review).

Restriction enzymes (restriction endonucleases) recognize specific short sequences of DNA (usually unmethylated DNA) and cleave the duplex molecule, usually at the target recognition site, but sometimes elsewhere. In some instances, the recognition site is specific, but the cleavage site is located some distance away from the recognition site and does not appear to be at any specific sequence.

"Duplex" refers to the double stranded composition of the DNA molecule. The cleavage induced by endonucleases is usually at specific sequences of approximately 4–6 base pairs. A base pair is a union of purines or pyrimidines in the DNA duplex. There are four such bases and they pair in specific unions: adenine with thymine, (A-T), guanine with cytosine (G-C).

Fragments generated by endonucleases are amenable for further analysis of their nucleotide composition. Variation in the fragment sizes obtained from the same chromosomal locations among individuals, is referred to as restriction fragment length polymorphism (RFLP).

Restriction endonucleases are essential components of methods used to construct maps of the genetic material, although not all such endonucleases are useful. Some of the problems limiting their use are that cleavage may be too frequent using a particular enzyme, producing pieces too small to be useful. Another problem is that the sites attacked may have nucleotide sequences that are so unusual that they are not likely to occur in vivo. Some enzymes only cleave artificially engineered sequences.

Restriction endonucleases are named by using three or four letter abbreviations identifying their origin, coupled with a letter and/or number designation which distinguish multiple enzymes of the same origin. An example of the nomenclature is EcoR1, one of the endonucleases derived from E. coli. Most of the endonucleases discovered initially were isolated from bacteria, in which they cleave DNA as part of the natural function of the cell. However, other organisms, for example, yeast, can be used as a source of double-strand DNA cleaving endonucleases.

Isolation of many endonucleases occurred because the bacteria from which the endonucleases were derived were able to distinguish between the DNA native to the bacteria and any invading foreign DNA. One of the ways bacteria recognized foreign DNA was by the absence of methyl groups at appropriate base pair sites. The bacteria protects its own DNA from cleavage by its own endonucleases, by methylation of its own DNA bases at appropriate target sites. Successful attack on bacteria by foreign DNA, for example by phage, may be due either to the fact that the phage DNA has the same pattern as the host DNA, or alternatively, that mutations have caused defects in the ability of the bacteria to produce an endonuclease or to attack the foreign DNA. Endonucleases isolated from bacteria are of two types, one which is only able to cleave DNA, and another in which both restriction and methylation activities are combined. Some restriction endonucleases introduce staggered cuts with overhangs others generate blunt ends.

(B) Restriction Mapping

Gene maps give the location of specific genes (specific DNA nucleotide sequences) that encode the primary sequences of protein gene products relative to each other and also localize the genes on specific chromosomes of higher organisms. A map of DNA obtained by using endonucleases to map breakpoints is called a restriction site map and consists of a linear sequence of cleavage sites. This physical map is obtained by extracting DNA from the chromosomes in cells, breaking the extracted DNA at various points with endonucleases, and determining the order of cleavage sites by analysis at the fragments.

Distances along the maps are measured directly in base pairs, or, if distances are long, in megabase pairs. By comparing the sequences of DNA between relatively short distances, a DNA map is constructed in a stepwise fashion. A major goal of current research is to construct a map of the entire human genome. (The Human Genome Project, American Society of Human Genetics Symposium, Baltimore, Nov. 15, 1989.) Success in mapping human and animal genomes will require a selection of endonucleases which cleave at a large variety of sites which occur in the DNA of living organisms, not just in artificial sequences.

DNA fragments produced by the action of endonucleases are separated on the basis of size by agarose or polyacrylamide gel electrophoresis. An electric current is passed through the gel, causing the fragments to move down it at a rate depending on length; the smaller fragments move more rapidly. The result of this migration in a gel, is a series of bands each corresponding to a fragment of a particular size. Many different endonucleases are used for gene mapping, and large numbers of overlapping fragments are analyzed. Sequential cleavage using different endonucleases produces a series of larger fragments broken down into smaller fragments. A hierarchy is then constructed based on the fact that there is complete additivity of length of the fragments within the original starting fragment. For example, a fragment of 2,100 base pairs may be broken down into 200 and 1900 base pairs. (see Lewin, 1987 for review).

Construction of an entire gene map for a species, for example construction of the human gene map, is a difficult and tedious task. The larger the number of endonucleases available for restriction mapping, the easier and more sophisticated the genetic map construction. In particular, many endonucleases are needed which cleave at a variety of specific sites and which produce fragments of different lengths. To appreciate the magnitude of the mapping problem it should be noted that an estimated 3 billion base pairs contained in 22 pairs of human chromosomes called autosomes plus two sex chromosomes, comprise the human genome.

Restriction maps represent advantages over older methods of mapping which identified a series of genetic sites because of the occurrence of DNA changes (mutations), because restriction maps can be obtained for any sequence of DNA. Their construction is not dependent upon the location of mutations, and no knowledge of the function of a particular sequence of DNA is required. However, restriction maps are related to, and are colinear with, "genetic" maps.

Mutations which are deletions or insertions of base pairs may be detected in restriction maps by noting an alteration of the length of a restriction fragment in which the mutation lies. Base-pair change type of mutations may be detected if their presence inactivates or creates a cleavage site of a particular endonuclease, altering the length of the restriction fragments produced by cleavage in the area of DNA in which the mutation lies.

(C) Restriction Fragment Length Polymorphisms (RFLP)

Different alleles (conditions of a gene) may lead to the production of different proteins and subsequent variation in the phenotype, (the detectable physical, biochemical, or physiologic makeup of the organism). Variation of DNA within populations is called genetic polymorphism. Even if the polymorphism does not lead to detectable changes in the phenotype by physical appearance or biochemical assays, genetic polymorphism may be detectable by variations in the DNA restriction fragment lengths (RFLP). Polymorphic variation in the restriction map therefore is independent of gene function.

RFLP's have numerous applications including as markers for paternity testing or determining the location of specific genes. For example, mutant genes responsible for inherited diseases such as Huntington's Chorea, a progressive neurological degeneration, have been localized to specific chromosomes in humans by correlating inheritance of RFLP's in families with the inheritance of the particular clinical condition. RFLP patterns of family members who are normal are compared with patterns of family members who are affected with a particular genetic disease.

(D) Other Uses for Restriction Endonucleases

Another use of restriction endonucleases is to create and use cloning vectors for the transmission of DNA sequences. For this purpose, the gene of interest needs to be attached to the vector fragment. One way this may be accomplished is by generating complementary DNA sequences on the vector and on the gene of interest so that they can be united (recombined). Some restriction endonucleases make staggered cuts which generate short, complementary, single stranded "sticky ends" of the DNA. An example of such an action is that effected by the EcoR1 endonuclease which cleaves each of the two strands of duplex DNA at a different point. These cleavage sites lie on either side of a short sequence that is part of the site recognized by the endonuclease. When two different DNA molecules are cleaved with EcoR1 the same sticky ends are generated which enables them to combine with each other. The DNA fragment can then be retrieved by cleaving the vector with EcoR1 to release the gene.

(E) Exons and Introns

The restriction map of DNA may not correspond directly with the coding sequence of messenger RNA produced by the DNA because DNA sequences of the total gene may consist of exons and introns. Exons are that part of the DNA code that appear in the messenger RNA. Most, but not all, exons code for proteins. Introns are DNA sequences that are usually spliced out of the RNA product before the messenger RNA proceeds to be translated into proteins. Splicing consists of a deletion of the intron from the primary RNA transcript and a joining or fusion of the ends of the remaining RNA on either side of the excised intron. Presence or absence of introns, the composition of introns, and number of introns per gene, may vary among strains of the same species, and among species having the same basic functional gene. Although in most cases, introns are assumed to be nonessential and benign, their categorization is not absolute. For example, an intron of one gene can represent an exon of another. A mosaic gene is defined as one which is expressed through the splicing together of exons carried by one molecule of RNA. In some cases, alternate or different patterns of splicing can generate different proteins from the same single stretch of DNA (Lewin, 1987).

(F) Mitochondrial DNA: Yeast Mitochondria

The DNA contained in mitochondria (cell organelles which contain extranuclear DNA) represents an example of differences arising during evolution between the composition of genes with regard to the exon and intron sequences as well as non-coding sequences. For example, comparing the mitochondrial genes of yeast with those in mammalian systems, indicates that identical mitochondrial proteins are produced despite the disparity in evolution between these species. The yeast mitochondrial genomes, however, are much larger than those occurring in vertebrates due to the absence of introns in the latter and the presence of non-coding spacer DNA in the former.

Primary DNA sequence data are known for many yeast isolates (see deZamaroczy and Bernardi, 1986) in which interstrain differences are due to (i) a small number of large deletions/additions, mainly concerning introns; (ii) a large number of small (10-150 bp) deletions/additions located in the intergenic sequences; (iii) 1-3 bp deletions/additions and point mutations. In *Saccharomyces cerevesiae* the size of mitochondrial DNA can range up to about 84 kilobases, approximately ⅔ of which is non-coding regions. There are more than 20 mitochondria per cell, i.e., approximately 4 genomes per mitochondrion. In comparison, vertebrate mitochondrial DNA is approximately 17 kilobase pairs. In the individual mitochondrion there are usually several copies of a single molecule of DNA. Moreover, there are multiple mitochondria per cell. In plants and some unicellular eukaryotes, extranuclear DNA is found in chloroplasts and mitochondria.

The DNA within the mitochondria directs protein synthesis, just as nuclear DNA does. However, a finite number of proteins are produced. There are general similarities in the machinery for gene expression in mitochondria of various species, rendering products and information derived in one genus applicable to many others. For some products, the cytochrome c oxidase in yeast, for example, protein synthesis combines factors produced in the cytoplasm encoded by nuclear DNA with those synthesized directly in the mitochondria. Mutations identifying almost all the mitochrondrial genes have been detected. Nuclear mutations that interact with, or abolish, the effects of these mutational complexes in the mitochondria, have also been found. Genes coding for many of the same functions are present both in the yeast and the mammalian mitochondrial genome, making the yeast mitochondria a good model system for testing theories on gene expression in higher organisms. The mitochondrial genome of one of the yeast strains, Saccharomyces cerevisiae has provided both information on genetic expression, as well as products which can be useful for analysis of higher systems. (Lewin, 1987; Butow 1985).

In the invention described herein, a new and unique restriction endonuclease has been isolated and purified. One obstacle to purification and characterization of this enzyme in the past has been the inability to accumulate sufficient amounts of the protein, a problem which has been solved by methods disclosed in this invention. A preferred source of the endonuclease described in this invention is yeast mitochondria from a special strain. The endonuclease has wide applications for in vivo or in vitro cleavage of double-stranded DNA from many genera.

SUMMARY OF THE INVENTION

Figure 2:
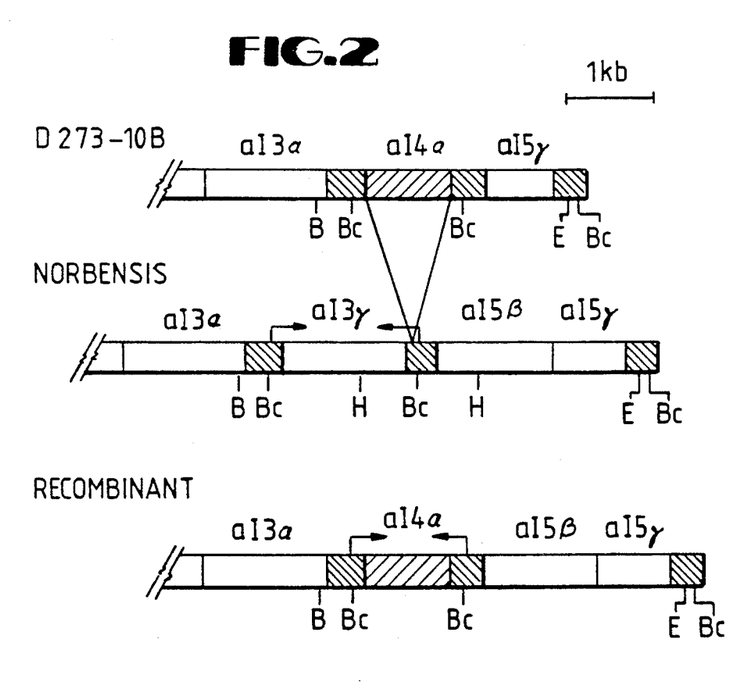
FIG. 2: Intron configurations of the cox1 gene.
Figure 3:
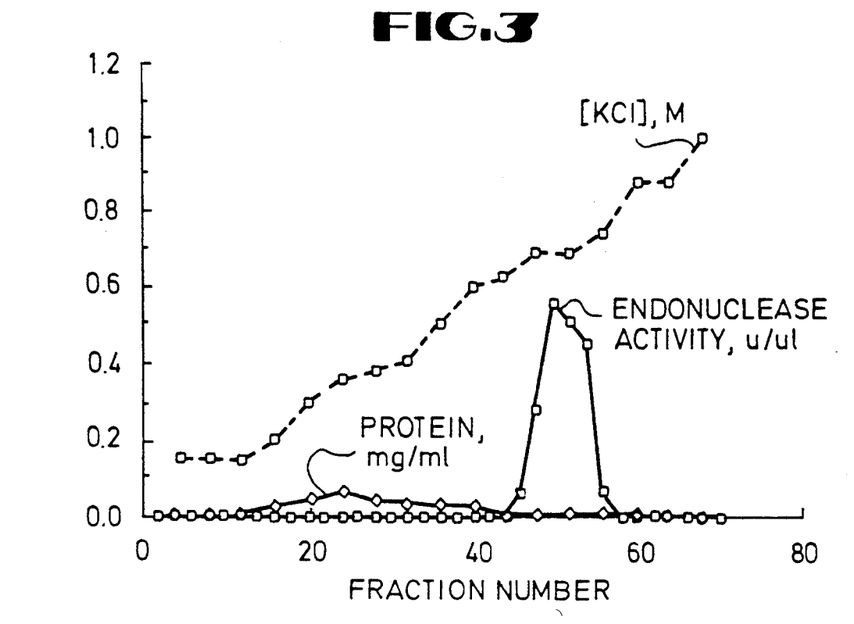
FIG. 3: Purification of the restriction endonuclease by phosphocellulose chromatography.

This invention is directed towards a substantially purified endonuclease preparation having an apparent molecular weight of 29,000 daltons as determined by SDS polyacrylamide gel electrophoresis. This endonuclease is capable of cleaving double-stranded DNA at specific sites (FIG. 2). Within these sites, certain specific nucleotides are essential for cleavage, as indicated in FIG. 2; at other sites, base substitution is compatible with cleavage.

The endonuclease described in this invention is further defined as having a biological activity of up to about 100 units/mg of protein in the crude extract. One unit of endonuclease activity is defined as that amount of enzyme that catalyzes the cleavage of 50 ng of a DNA molecule in one hour at 30° C., although other definitions of activity would be within the scope of this invention.

Purification of the endonuclease by standard protein purification techniques was accompanied at each sequential step by increased activity of the endonuclease. Specific examples comprise a biological activity up to about 34,000 units/mg after phosphocellulose chromatography; 50,000 units/mg after Affigel Heparin chromatography; 200,000 units after gel filtration; and 500,000 units/mg after DNA affinity chromatography (FIGS. 3–6, Table 1).

Figure 7:
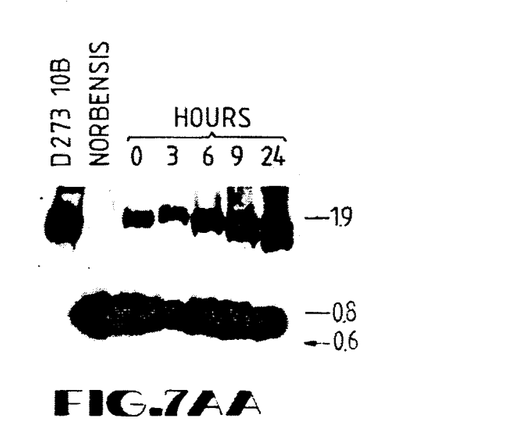
FIG. 7: In vivo double-stranded cuts in recipient DNA molecules.
Figure 7A:
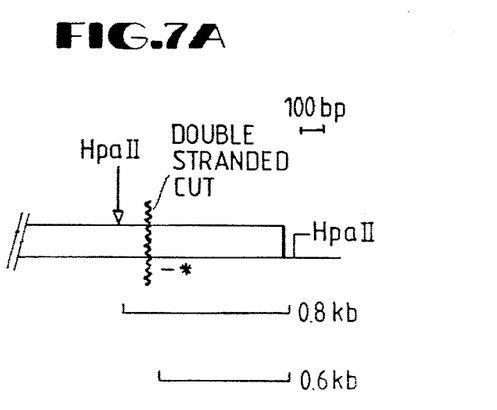
Figure 7B:
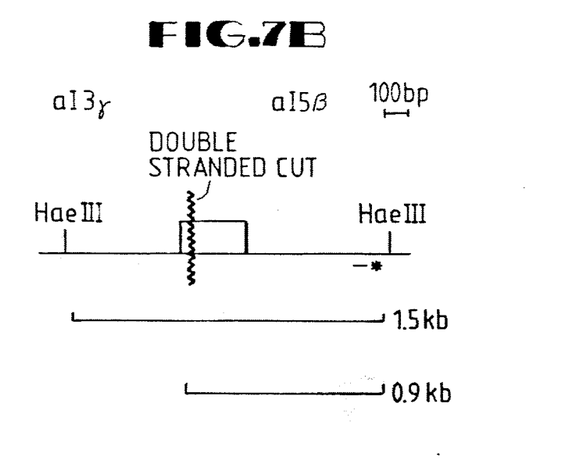
Figure 8:
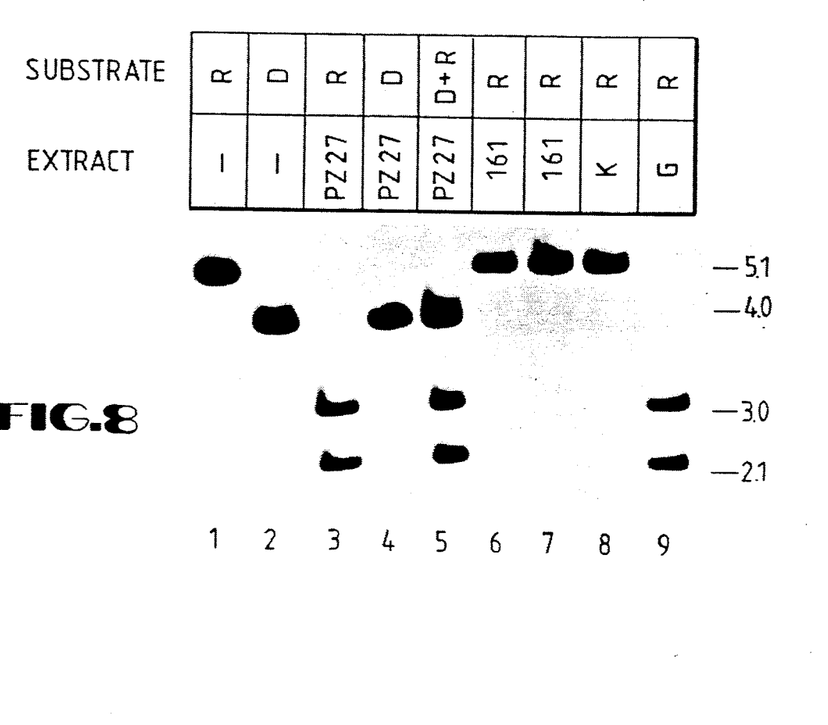
FIG. 8: Mitochondrial extracts contain an endonuclease that cleaves recipient DNA near the site of intron insertion.

The endonuclease is translated from a fusion between the upstream exons of the mitochondrial cytochrome oxidase subunit I gene (cox1) of yeast (FIG. 1) and the open reading frame (ORF) within the 4th intron (aI4α) of the (cox1) gene. The endonuclease was capable of cleaving recipient DNA molecules near the site of yeast mitochondrial cox1 aI4α intron insertion (FIGS. 7–8). The endonuclease is also capable of acting as a maturase under certain conditions. Examples of such conditions include presence of a point mutation in the intron reading frame of the mim-2 mutation, (Dujardin et al., 1982) or the presence of the nuclear NAM2 gene (Herbert et al., 1988).

A preferred source of the endonuclease is mitochondria, more specifically yeast mitochondria. An object of this invention was to describe a method of isolating and purifying the endonuclease from yeast mitochondria, more specifically Saccharomyces cerevisiae mitochondria. The WA12 strain of yeast containing mtDNA derived from strain ID41-6/161/PZ27 was a preferred source.

A method is disclosed for preparing the endonuclease. The preferred embodiment comprises culturing yeast that are incapable of splicing the aI4α intron of the cox1 gene, thereby accumulating sufficient amounts of endonuclease to use for isolation, purification, and characterization. The method further comprises preparing mitochondrial extracts from yeast, fractionating the extracts, and selecting a fraction or fractions which contain the endonuclease disclosed in this invention. The endonuclease is further identified by its ability to cleave double stranded DNA at the specific site (underlined and demarcated by vertical lines on either side of the cleavage point):

Another object of this invention is a method of cleaving DNA. This method comprises preparing the endonuclease described herein, by the method disclosed in this invention, and incubating the isolated and purified endonuclease protein with DNA so as to effectuate the endonucleolytic cleaving of the DNA.

Other objects and advantages of the invention will become apparent upon reading the following detailed description and upon reference to the drawings in which aspects of the invention are illustrated.

BRIEF DESCRIPTION OF THE DRAWINGS

The cleavage site specificity of the endonuclease is shown. Boxed residues are those believed to be essential for cleavage. The nucleotides changes indicated above the non-boxed nucleotides, are those that have been tested and found to permit cleavage. It is possible that other nucleotides will be identified which can substitute at these positions. The enzyme cut sites are indicated by the vertical and the sticky end is indicated by the horizontal lines.

The cox1 gene of yeast mtDNA contains up to ten introns, three of which were found recently in cox1 genes from newly studied isolates (Kotylak et al., 1985; Ralph, 1986; Ralph et al., unpublished data). The intron configuration of this gene in strains D273-10B and S. norbensis Y-12,656, is shown in lines 1 and 2, respectively. The cox1 gene structure of a recombinant resulting from conversion of aI4α is shown in line 3. All three strains shown also contain introns aI1 and aI2. Because two of the new introns are present in strains used in this study, a new nomenclature for cox1 gene introns was used. Previously described introns 3 and 4 are renamed aI3α and aI4α, respectively. One new intron, located between aI3α and aI4α, is called aI3α (because another new intron, aI3β, is present between aI3α and aI3α in *S. douglasii* [Kotylak et al., 1985]). Exon sequences are indicated by dark boxes whereas introns are designated by open or shaded boxes. Arrows indicate regions sequenced as a basis for this invention. The asterisk denotes the location of two sequence differences between strains D273-10B and *S. norbensis* located in exon 5α. The abbreviations used are: B, BamHI; Bc, BclI; H, HaeIII; E, EcoRl (Wenzlau et al., 1989).

Fraction Ia (see Table I) was dialyzed ($M_r$ cutoff, 10,000) against ice cold buffer containing 50 mM potassium phosphate, pH 7.5, 10% glycerol, 2 mM EDTA, 2 mM DTT (Buffer A) until an ionic equivalent of approximately 100 mM KCl was achieved. The sample was loaded onto a phosphocellulose column (5 mg protein per packed ml of phosphocellulose), previously equilibrated at a flow rate of 20 ml/hour with Buffer A. The column was washed with 120 ml of Buffer A containing 200 mM KCl at a rate of 60 ml/hour and then a 240 ml linear gradient was applied using Buffer A containing 200 mM KCl and 1M KCl at a rate of 80ml/hour. The aI4α endonuclease activity eluted at 0.7M KCl. Active fractions were pooled (fraction II, Table I) and dialyzed against Buffer A until an ionic equivalent of 50 mM KCl was reached.

The dialyzed fraction II (Table I) having endonuclease activity and resulting from phosphocellulose chromatography (FIG. 3) was applied to an Affigel Heparin column, previously equilibrated with Buffer A (0.1 mg protein per packed ml of Affigel Heparin), at a rate of 2.5 ml/hour. The column was washed with 15 ml of buffer A containing 50 mM KCl at 7 ml/hour and eluted with a 60 ml linear gradient of Buffer A containing 100 mM KCl to 600 mM KCl at a rate of 15 ml/hour. The enzyme eluted at 300 mM KCl, and the active fractions were pooled (fraction III, Table I).

Fraction III (Table I, FIG. 4) was applied to a Sephacryl HS 200 column (1.4 cm×85 cm) equilibrated with Buffer A containing 100 mM KCl at a rate of 3.2 ml/hour. The column was calibrated with blue dextran 2000, B-amylase, yeast alcohol dehydrogenase, lactate dehydrogenase, bovine serum albumin, carbonic anhydrase and cytochrome c. The column was eluted with the Buffer A and 0.95 ml fractions were collected. Fractions containing aI4α endonuclease activity were pooled (fraction IV).

Fraction IV (Table I, FIG. 5) was applied to a DNA affinity column equilibrated with Buffer A containing 100 mM KCl at 1.5 ml/hour. The column was washed with 6 ml of the same buffer at 6 ml/hour and eluted with 18 ml of a linear gradient of Buffer A containing 100 mM KCl to 800 mM KCl at a rate of 9 ml/hour. The aI4α endonuclease activity eluted at 300 mM KCl. The active fractions were pooled and mixed with an equal volume of 50 mM potassium phosphate, pH 7.5, 80% glycerol and 2 mM EDTA and stored at −20° C. (fraction V, Table I).

A restriction fragment spanning the intron insertion site was examined for double-stranded breaks in mated cells. The strains 5DSS/D273-10B and COP-19/norbensis were mated, and mtDNA was isolated at the beginning of mating and 3, 6, 9, and 24 hr after mating began. The DNA was digested with either Hpa II FIGS. 7A and 7AA or Hae III FIGS. 7B and 7BB and analyzed to detect double-strand cuts near the sites of insertion for omega and aI4α, respectively. MtDNA was fractionated on 6% polyacrylamide gels, electrophoretically transferred to Hybond-N membranes, and hybridized to end-labeled oligonucleotides specific to 21S rRNA gene exon sequences FIGS. 7A and 7AA or to aI5β sequences FIGS. 7B and 7BB. A 0.6 kb fragment (arrow) corresponding to an in vivo double-stranded cut near th site of omega insertion was seen from 6-9 hr after initiation of mating in the HpaII digest FIG. 7A. Similarly, a 0.9 kb fragment (arrow) consistent with a double-stranded cut near the site of aI4α insertion was present from 6-9 hr after mating in HaeIII digests FIG. 7B.

Mitochondrial extracts were assayed for their ability to cleave recipient (R) or donor (D) DNA. Plasmids pDR1 (recipient) and pJW1 (donor) were linearized with EcoRl and 3' end-labeled. These substrates were incubated with mitochondrial extracts from wild-type strain ID41-6/161 and mutant derivatives PZ27, G, and K. Cleavage of pDR1 DNA at or near the site of intron insertion would yield products of 2.1 kb and 3.0 kb (lanes 3, 5, and 9). Cleavage of pJW1 DNA at the equivalent exon site would yield products of 1.2 kb and 2.8 kb. The substrate and extract used are indicated above each lane: 39 ng of extract protein from strain PZ27 was added to lanes 3, 4, and 5; 39 ng and 3 65 µg of extract protein from wild-type strain I41-6/161 was added to lanes 6 and 7, respectively; and 150 ng of extract protein from mutant K and 182 ng of extract protein from mutant G was added to lanes 8 and 9, respectively.

Single-stranded DNA from phages RS18 and RS19 was labeled using the Sequenase (United States Biochemical Corporation) protocol and the universal sequencing primer. This material was then extended either using dideoxynucleotides (to generate a sequencing ladder) or with unlabeled nucleotides (to generate the substrate). Substrate samples were cleaved with a mitochondrial extract from strain PZ27 (see FIG. 7). FIGS. 9A and 9B show the sequencing gels generated by this protocol using phages RS19 and RS18 as templates, respectively. In each panel, lanes 1-4 represent chain termination reactions with dideoxy G, A, T, and C, respectively; lane 5 is the product of a cleavage reaction on the "end-labeled" substrate; lane 6 shows this region of the gel using uncut substrate to demonstrate no premature primer extension products in the vicinity of the cleavage site. FIG. 1 shows the sequence surrounding the cleavage site (FIG. 1). Intron sequences are shown in lower case letters while exon sequences are in upper case letters. The large arrow indicates the point of intron insertion. The sites of cleavage on each strand are shown by small arrows. The exon sequences of donor and recipient are nearly identical; two differences in the exon between donor and recipient are shown by asterisks. The bracket sets an upper limit on the boundaries of the recognition site (based on the data of FIG. 10).

The recognition sequence was delimited by determining the extent of each sequencing ladder of FIG. 9 that was resistant to cleavage by the endonuclease activity. The products of sequencing reactions using phage RS19 as a template are shown in FIG. 10A, lanes 1–4 (terminated with dideoxy G, A, T, and C, respectively). These sequencing ladders were used as a substrate for cleavage reactions using 500 ng of protein extract from strain PZ27 in lanes 5–8. The ladder was resistent to cleavage until a recognition sequence was generated. All chains with further additions were efficiently cleaved. FIG. 10B shows the results of a similar experiment using RS18 as a template. Lanes 1–4 show the products of the sequencing ladder (terminated with dideoxy G, A, T, and C, respectively). In lanes 5–8, the products of the ladder were cleaved with extract from strain PZ27. The maximum boundaries of the recognition sequence are shown in FIG. 1.

TABLE I
SUMMARY OF PURIFICATION OF THE RESTRICTION ENDONUCLEASE

| | Sequential Purification Steps | Activity* U × 10$^{-3}$ | Yield | Protein (mg) | Specific Activity (U/mg) |
|---|---|---|---|---|---|
| I. | Crude Extract | 26 | 100 | 216 | 100 |
| Ia. | 40–60% (NH$_4$)$_2$SO$_4$ | 3 | — | 114 | — |
| II. | Phosphocellulose | 20 | 79 | 0.6 | 34,000 |
| III. | Affigel Heparin | 5 | 19 | 0.1 | 50,000 |
| IV. | Gel Filtration | 4 | 16 | 0.02 | 200,000 |
| V. | DNA Affinity | 1 | 4 | 0.002 | 500,000 |

*For purposes of this invention, one unit of endonuclease activity was defined as that amount that catalyzed the cleavage of 50 nanograms of DNA substrate in one hour at 30° C. Other definitions of activity are within the scope of this invention.

DESCRIPTION OF THE PREFERRED EMBODIMENTS

This invention is directed to a new and unique endonuclease, and to methods of preparing and using this enzyme.

Although other endonucleases have been discovered which cleave DNA at specific sites, there is clearly a need for more endonucleases, in particular those with special and useful properties, to facilitate gene mapping. The endonuclease described herein has the capability of producing relatively larger fragments of DNA and also to act on restriction sites (cleavage sites), that are commonly encountered in the genome. Some enzymes operate only on unusual sequences, e.g., only GC base pairs.

The general objective of this invention is to purify and apply a new endonuclease protein with useful characteristics not previously available to the art. Prior to the invention described herein it had not been possible to isolate and purify the endonuclease protein so that its sequence and function could be analyzed.

The endonuclease which is disclosed by the current invention will cleave ordinary DNA sequences. Use of this endonuclease for gene mapping will facilitate and expand the resolution of determination of DNA sequences within fragments cleaved by the endonuclease.

In one of the preferred embodiments, the endonuclease as extracted from mitochondria of strain WA12/PZ27 yields a biological activity of up to about 100 units/mg per protein. These mitochondrial extracts further processed by phosphocellulose chromatography, resulted in the purity increasing to 34,000 units/mg. Application of Affigel ® heparin chromatography increased the purity of the endonuclease up to about 50,000 units/mg. Fractionation by gel filtration yielded a biological activity of 200,000 units/mg. Further purification by DNA affinity chromatography yields a biological activity of 500,000 units/mg (FIGS. 3–6). The purified protein has an estimated molecular weight of 29 kilodaltons as determined by SDS-PAGE.

A maximum of 14 base pair sites are believed to be required for cleavage. There are at least four residues known to be essential for the cleavage; in other positions, some substitutions are permitted and cleavage will still occur (FIG. 1).

Figure 1:
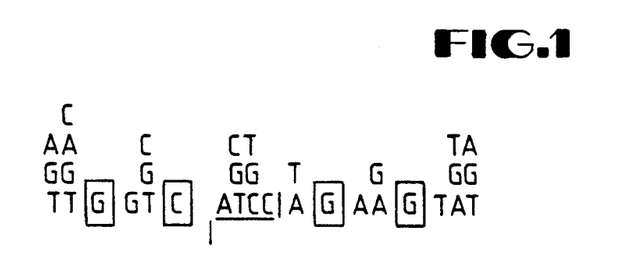
FIG. 1: The DNA cleavage site of the aI4a encoded endonuclease.

As can be seen in FIG. 1, the 3' and 5' ends of the 18 base pair recognition sequence are highly variable, thus at least 14 base pairs of this site are apparently required for recognition of the cleavage site.

Most of the endonucleases discovered to date have been from bacterial systems, and most are expressed in E. coli, because it is more difficult to purify endonucleases from more complex systems. This limitation was also due to the fact that bacteria are capable of producing quantities of a specific protein in large enough amounts to provide material on which purification procedures may be employed.

The mitochondrial genomes of many yeast species have been mapped and shown to contain both introns and exons. (deZamaroczy and Bernardi, 1986) Two of the most informative loci for genetic investigations are the mosaic genes cob (which codes for cytochrome b) and oxi3 (which codes for subunit I of cytochrome c oxidase. Many of the introns in these two genes have open reading frames, sequences which are read as extensions of the exon immediately preceding it. An unusual circumstance is that most introns in mitochondrial yeast genomes may be expressed as proteins.

In common with yeast, the mammalian systems have genes for cytochrome b, cytochrome oxidase and subunits of ATPase. The known mitochondrial gene products vary little among eukaryotes as diverse as fungi and vertebrates. The yeast mitochondrial genome consists of large numbers of conserved DNA sequences plus interruptions by an assortment of so-called optional sequences. The genome of a given yeast strain appears to be very stable. Coding sequences among strains are conserved, but optional sequences are present or absent at various positions in many combinations. The wide range of functional combinations of introns arose during speciation of yeast. Further combinations of those probably arose in laboratory strains by unselected mitochondrial recombination during the many decades of genetic manipulation in which current laboratory strains were derived (Butow, 1985). The operational definition of optional sequences is that the presence or absence of these sequences do not affect phenotypic expression of the exon coding region.

Much has been learned about the mechanism of RNA splicing by examination of yeast systems. RNA splicing normally removes the introns from the transcripts of genes by breaking the phosphodiester bonds at the exon-intron boundaries, and subsequently forming bonds between the ends of the free exons. There are various mutants of yeast which are unable to splice the introns; therefore the precursors accumulate in the cells. This can occur in either the nucleus or the mitochondrial genes or both. The mitochondrial introns in yeast may be divided into two types, group 1 and group 2. Group 1 introns appear to have a common secondary structure, short conserved sequences internally, but no specific conservation of sequences at the splice junctions. Some of these introns, for example, those in cox1 and the large mitochondrial ribosomal RNA gene of *Saccharomyces cerevisiae*, are self-splicing. Mutations in other genes, however, can affect the occurrence of splicing. In both group 1 and group 2 there are some introns which must translate an extensive coding sequence to splice the intron containing it. Some introns encode a protein involved in splicing, called RNA maturases. Maturases appear to result from translation of both exons and introns.

Both homologous and non-reciprocal mitochondrial recombinations occur in genetic crosses of yeast. Non-reciprocal exchanges involving some optional sequences have been reviewed by Butow (1985). The best characterized system of non-reciprocal exchange analyzed in yeast is the omega system. Omega is a 1.1 kb optional intron in the 21S rRNA gene. In genetic crosses between omega positive and omega negative yeast, the progeny are usually omega positive. That is, there seems to be unidirectional transfer of the intron. Mutants lacking this polarity of transfer occur either as base changes close to the site where the intron would be inserted, or as mutations in the intron reading frame preventing its translation. The protein product of the omega intron is not involved in omega splicing.

The hypothesis generated from studying the omega system is that the protein coded by the intron in the omega positive strain (fit/or omega transpose) recognizes the DNA site where the intron should be inserted in an omega negative strain. This causes it to be preferentially inherited. The protein coded by the omega intron has endonuclease activity recognizing a specific sequence in the omega negative gene as a target for cleavage of the double-stranded DNA (Jacquier and Dujon, 1985; Colleaux et al., 1986). The recognition site lies at the site where the intron is inserted. The double-strand break probably initiates what is called a gene conversion, a process in which the sequence of the omega positive gene is copied and replaces the sequence of the omega-negative gene.

Cleavage of intronless (omega-negative) DNA near the site of intron insertion is required for conversion, and it is believed that introns carrying sequences which accomplish gene conversion may have once been independent elements that coded their own splicing or interacted with the DNA of the recipient strain. This creates a transposable element (transposon). Finding that such gene conversions are required for cleavage of the recipient DNA by a site-specific endonuclease, leads to the expectation that isolation and purification of such endonucleases would prove extremely valuable not only in understanding the genetic mechanisms of these conversions but also could provide a valuable reagent for gene mapping studies.

When two parental strains having distinguishable mitochondrial DNAs are mated, the progeny are expected to represent the parental DNA in some aspects. Recombination refers to the new union of DNA present in separate parents, in a single progeny DNA. Mitochondrial DNA from different parental strains is capable of recombining.

Through studies of gene conversion in yeast mitochondria, it has been determined that one of the mechanisms achieving gene conversion employs an endonuclease aI4α which cleaves the recipient DNA at specific sites (Wenzlau et al., 1989). For one of these endonucleases, the aI4α-encoded protein, there exist, however, yeast strains that overproduce or overexpress the enzyme relative to wild-type yeast strains because of various mutations of the yeast mitochondrial genome. An example of such a strain of yeast is the WA12 strain containing the PZ27 mutant mitochondrial DNA of *Saccharomyces cerevisiae*. Strain PZ27 was isolated in 1978. In the mitochondrial genome of this strain the cytochrome oxidase gene (cox1) is present, but the cytochrome b gene is deleted. This configuration blocks splicing of aI4α causing the protein encoded by that intron reading frame to be present at high levels in mitochondria. This protein is a site-specific endonuclease that is translated from a fusion between the upstream exons of coxI and the open reading frame within the intron aI4α. All yeast have the cox1 gene, and most contain intron aI4α. A few strains, however, have lost the capability of splicing the intron, leading to overproduction of an endonuclease.

In wild-type yeast strains splicing of this intron 4α is assisted by a product of the fourth intron of the cytochrome b gene called the bI4 maturase. Splicing would normally remove the intron. However, there are several strains in which there is an inability to splice aI4α resulting in an accumulation of the endonuclease produced by that region of DNA. This overproduction occurs, for example if there are mutants at the bI4 locus or deletions of the bI4 reading frame. In strain WA12 containing mDDNA from strain PZ27 there is a deletion of the cob gene, consequently a deletion of intron bI4, leading to continued production of the endonuclease produced by the coxI gene because there is no splicing of the intron. Otherwise the strain has a wild-type coxI gene based on complementation studies.

Some other strains exist with defects in the bI4 maturase that would lead to this overproduction. In fact any strain with the inability to splice out aI4α will lead to overproduction of the endonuclease. A preferred embodiment is to use the WA12 strain as a source of crude extracts of mitochondria. After culturing the yeast, mitochondrial extracts can be prepared by standard methods of lysing cells and fractionation. These extracts can be further purified by being subjected to phosphocellulose chromatography, affigel heparin chromatography, gel filtration and DNA affinity chromatography. Any other suitable methods of purification of proteins known to those skilled in the art may be applied.

The endonuclease described herein was capable of cleaving double-stranded DNA at a specific site to achieve gene conversion in recipient strains. (FIGS. 7-8). It also has the potential to become a maturase under certain conditions. A maturase is an intron-encoded RNA splicing protein. It has been reported that the maturase coded in yeast by the fourth intron of the cytochrome b gene (bI4) is essential for splicing the fourth intron of the gene encoding subunit 1 of the cytochrome c oxidase (coxl gene). The cox1 intron 4α encodes a protein that is closely related structurally to the bI4 maturase, but in wild-type yeast strains is not utilized in splicing either the fourth intron of cox1 or cob. However, the aI4α product can be activated to a new maturase form by either a point mutation (mim-2) (Dujardin et al., 1982) or the presence of the NAM2 gene (Herbert et al., 1988).

Figure 10A:
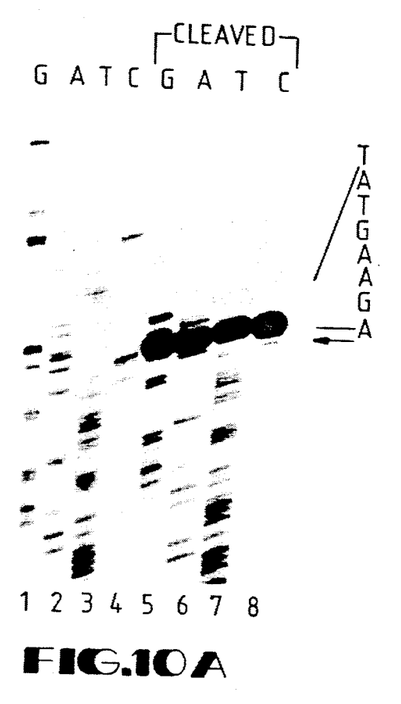
FIG. 10: Location of the recognition sequence of the al4α-encoded endonuclease.
Figure 10B:
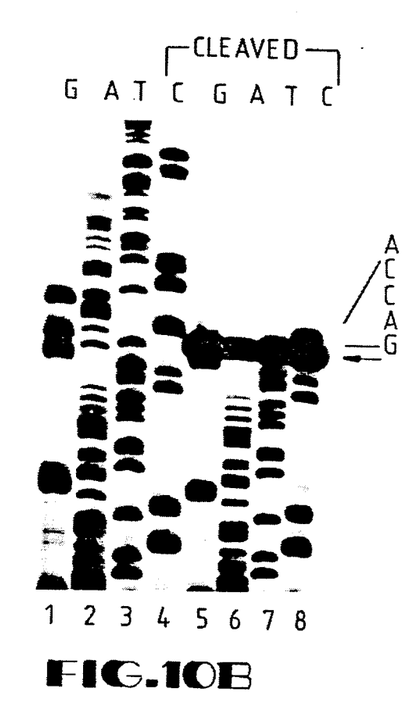

Although intron-encoded endonucleases have not previously been isolated and purified from yeast mitochondria, the use of special laboratory strains in this invention which continue to produce these products due to lack of splicing, permitted the isolation of endonucleases in amounts sufficient to be isolated, purified and characterized. The function and structure of one of these endonucleases was determined for the first time as an aspect of this invention because of the increased amounts obtained from the special strain WA12/PZ27 of *Saccharomyces cerevisiae*. The specific site cleavage of double-stranded DNA was determined by presenting known sequences of DNA of different lengths to the endonuclease and studying the resulting cleavage products. A partial recognition site determination is shown in FIG. 10.

The purified fraction is then selected which comprises an endonuclease capable of cleaving DNA at specific sites. This capability can be tested by various assays. The cleavage site, plus flanking DNA sequences can be introduced into various plasmids to use as an in vitro assay. Essentially any plasmid DNA containing the cleavage site will be suitable. In a preferred embodiment the assay used comprised a plasmid pRSX which contains a 292 base pair, RsaI-HindIII fragment that includes the cleavage site from *Saccharomyces capensis* cloned into the vector PBS(+) from Stratagene.

Two assays were used to determine the activity of the endonuclease:

1. A supercoiled DNA preparation of pRSX was incubated with the endonuclease, and cleavage activity was determined by gel electrophoresis of the subsequent fragments. If cleavage has occurred there will be conversion of the supercoiled DNA to the linear form of the plasmid which can be determined by gel electrophoresis;
2. pRSX DNA was linearized with ScaI. Using standard techniques the linear plasmid was end-labelled, extracted, and endonuclease activity was determined by the production of two radioactive fragments after incubation with the enzyme for which activity is to be determined.

An object of this invention is to cleave DNA at specific sites. Determining whether this was achieved by preparing the endonuclease protein as defined above, was done by incubating the enzyme with DNA so as to effectuate the cleaving of DNA.

Strains shown in FIG. 2 were used in crosses to study the transmission and recombination behavior of three group 1 introns of the cox1 gene. The data shown in FIG. 7 indicated that the mated cells contain an endonuclease activity capable of cleaving recipient genomes in the vicinity of the site of conversion. Experiments employing petite mutants of yeast which do not express mitochondrial genes, showed that no conversion occured in petites. The conclusion from these studies was that a product of mitochondrial protein synthesis is needed for aI4α conversion. Results of crossing strains of yeast differing in their intron configuration of three mosaic genes (cox1, cob. 21SrRNA), and use of various strains having point mutations of aI4α, led to the conclusion that the aI4α intron likely encodes the information needed for aI4α conversion. The aI4α reading frame must be intact to effect conversion.

In this invention, purification and subsequent application of an enzyme not previously purified, was achieved and found to cleave DNA as shown in FIG. 1. The endonuclease appears to require $Mg^{2+}$ at a concentration of about 25 mM for activity and shows high activity at pH 7.5 in the presence of 200 mM salts of monovalent cations. Activity does not appear to be stimulated by the addition of nucleoside triphosphates (see also FIG. 8). Other properties of the endonuclease illustrated in FIG. 8 are: lane 3; the mitochondrial extract from strain PZ27 cleaves the recipient plasmid once near the intron insertion site (this linear product can be circularized by DNA ligase); lane 4: donor DNA is not cleaved: lane 5: only recipient DNA is cleaved; lanes 6 & 7 show that cleavage activity is not detected in extracts of mitochondria from a wild-type strain capable of efficient splicing of aI4α; lane 8: no cleavage using extract from an aI4α mutant with a truncated intron ORF; lane 9: cleavage from an extract of an aI4α mutant with an intact intron ORF.

The endonuclease has been shown to be active in *E. coli* by use of an artificially engineered sequence of the endonuclease coding sequences in a transforming vector, using the universal genetic code. However, it is highly toxic in *E. coli* probably due to its cleavage of double stranded *E. coli* DNA (Delahodde et al., 1989).

A major advantage of the purified endonuclease, is that it cuts DNA relatively infrequently, and consequently is particularly useful for genome mapping. If all 14 nucleotides are required for cleavage, then one can estimate 1 to 2 cleavage sites per human chromosome. However, because there is some relaxation in the specificity of the cleavage site, empirical tests leading to actual determination of cuts effected by the endonuclease in clonal portions of human chromosome number 3, show one site about every 200 kilobase pairs.

Since the DNA sequence which the inventors have discovered to encode for the endonuclease is available, it could be engineered for expression in, e.g., *E. coli*, (Bonitz et al. 1980 and Delahodde et al. 1989). However, the preferred embodiment is to prepare this endonuclease from yeast mitochondrial extracts because of possible variations in the protein during the course of molecular engineering and expression in other species and because of its apparent toxicty to bacterial cells.

A major current scientific project is to map the entire human genome. This is a laborious, labor-intensive, and difficult task which will be facilitated by use of the endonuclease described in this invention. Human gene mapping permits detection of carriers of abnormal genes, and isolation and cloning of genes which cause abnormal human conditions. A goal of the mapping project is further elucidation of gene action, paving the way for therapy. Complete mapping of the human genome will also contribute to the field of preventive medicine by making it possible to determine the susceptibility of individuals to specific genetic disorders. Because the phenotype (expression of such genes) represents the interaction between genes and environment, preventive action based an knowledge of the genetic complement of the individual may be achieved by altering their environment (diet, drug, medication) to reduce or eliminate the severity of the abnormal genetic defects. The ultimate goal, of course, is to identify these genes so that direct gene therapy will be possible. If the genomic sequences are known, then normal genes may be directed into the genotype, perhaps at early stages of development, to counteract the effects of abnormal genes. A further goal of gene mapping is to understand the interaction and interrelationships of genes on different parts of the chromosome and on different chromosomes.

The purification, isolation and use of the endonuclease which is an object of this invention are further described in the following examples:

EXAMPLE 1

Yeast Strain

Purification of the endonuclease is made possible by the use of a strain or strains that overproduce the enzyme. In wild-type yeast strains, splicing of aI4α is assisted by the "maturase" product of the fourth intron (bI4) of the cytochrome b gene (cob); mutants of the bI4 maturase, or deletions of all or portions of the bI4 reading frame, result in a block in splicing of aI4α. Because the mRNA for aI4α endonuclease is a fusion of the intron reading frame with those of the upstream exons, the inability to splice aI4α results in an accumulation of the endonuclease mRNA and, hence, an overproduction of the protein. Therefore, to facilitate purification of the endonuclease protein, a strain (WA12), containing the mutant mitochondrial genome, PZ27, which is deleted for the cob gene, is used. (Note, however, that any strain with a defect in the synthesis of the bI4-encoded maturase would overproduce the aI4α endonuclease and therefore be suitable as a starting strain for purification.) a deposit of yeast strain WA12 (a,NUC1:-:LEU2,ura,trp,ad,bis,PZ27) has been deposited under the rules of the Buadpest Treaty on the international recognition of the deposit of microorganisms for the purposes of patent procedure and pursuant to the Manual of Patent Examining Procedure, Section 608.01(p)C. The American Type Culture Collection Designation for this strain is 20973.

EXAMPLE 2

DNA Cleavage Site

Figure 9A:
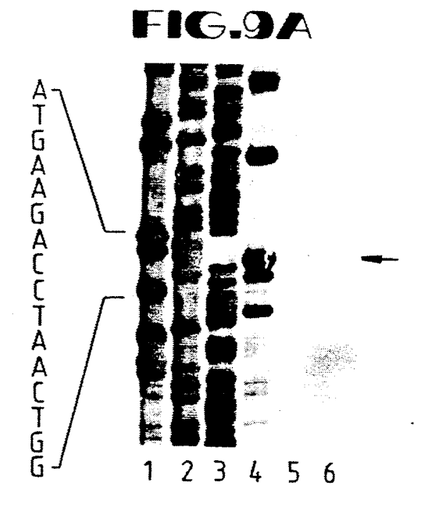
FIG. 9: Preliminary cleavage site determination of the endonuclease.
Figure 9B:
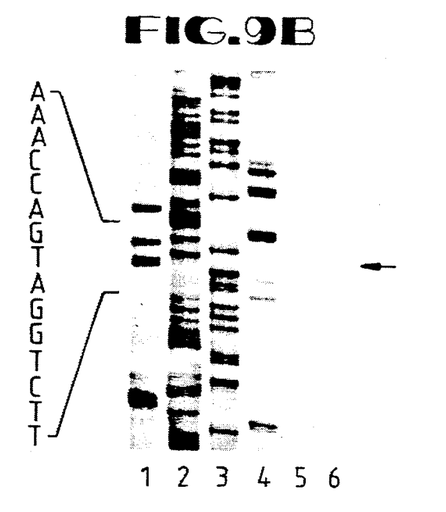

The cleavage site for the endonuclease is the sequence shown in FIG. 1. This site is cleaved with high efficiency by crude and purified preparations of the endonuclease which catalyzes a 4 bp staggered double strand break as shown in FIG. 1, leaving 3' OH overhangs. Preliminary determination of the cleavage site is shown in FIG. 9. The boundaries of the recognition site are shown in FIG. 10. Methods are detailed in Wenzlau et al., 1989.

EXAMPLE 3

Assays for Endonuolease Activity

For an in vitro assay of endonuclease activity, the cleavage site shown in FIG. 1, plus flanking DNA sequences was introduced into various plasmids. Essentially any plasmid DNA containing the cut site is suitable. For the assays described herein, the plasmid pRSX containing a 292 bp Rsa I—Hind III fragment that includes the cut site from *S. capensis* cloned into the vector pBS (+) from Stratagene was used.

Two assays were conveniently used to follow enzyme activity:

a) Cleavage of supercoiled DNA. A supercoiled preparation of pRSX was incubated with the endonuclease under the assay conditions described below, and cleavage activity was evident, following gel electrophoresis of the sample, as a conversion of the supercoiled to the linear form of the plasmid;

b) Linearization and end-labelling of pRSX. pRSX DNA was linearized with ScaI. After phenol extraction and ethanol precipitation, the linear plasmid was end-labelled with $^{32}P$ dATP and T4 DNA polymerase by standard procedures. The labelled DNA was then extracted by phenol and the unincorporated dNTPs were removed by gel filtration. The radioactive pRSX DNA was ethanol precipitated and resuspended in sterile water. Endonuclease activity was followed by the production of two radioactive fragments following incubation with active enzyme.

The endonuclease assay conditions used were as follows: Reaction mixtures (0.025 ml) contained 25 mM Tris-HCl, pH 7.5, 20 mM $MgCl_2$, 100 mM KCl, 2 mM DTT and 100 ng pRSX plasmid DNA. Incubation was carried out at 30° C. for 30 minutes. Reactions were stopped by being placed on ice and a 1/10 volume gel loading buffer was added. The samples were analyzed by electrophoresis in 0.7% agarose gels containing 1 μg/ml ethidium bromide. For purposes of this invention, one unit of endonuclease activity was defined as that amount that catalyzes the cleavage of 50 ng of the DNA substrate in one hour at 30° C. Other definitions used in the art would be consistent with this invention.

EXAMPLE 4

Protocol for the Purification of the Endonuclease (a) Preparation of Crude Mitochondrial Extract and Ammonium Sulfate Fractionation A *Saccharomyces cerevisiae* strain (WA12/PZ27) was grown in medium composed of 1% yeast extract, 1% bacto-peptone and 2% galactose to late log phase at 30° C. The cells were collected by centrifugation, washed with 2 mM EDTA, at pH 8, and resuspended at 2 ml/g, wet weight, in buffer containing 33 mM potassium phosphate, pH 5.8, 1M sorbitol and 2 mM EDTA. Mureinase was added at a ratio of 4 mg/g, wet weight, and the mixture was incubated on a platform shaker at room temperature for one hour. Spheroplasts were collected by centriguation at 1000 x g for 10 minutes at 3° C. and resuspended in ice cold breakage buffer which contained 50 mM Tris-HCl, pH 7.5, 0.6M sorbitol, 2 mM EDTA, 2 mM DTT and protease inhibitors (which were also included in all subsequent steps of the purification): PMSF (1 mM), leupeptin (1 μg/ml) and aprotinin (1 μg/ml). Spheroplasts were lysed by shaking with glass beads. The lysate was recovered and the glass beads were washed 3 times with breakage buffer. The combined spheroplast lysate was centrifuged at 1000 x g for 10 minutes at 3° C.

A high salt extract of the crude supernatant was prepared by addition of 0.33 volume of 4M KCl to achieve a final concentration of 1M KCl. $MgCl_2$ and DTT were added to final concentrations of 10 mM and 2 mM, respectively. The high salt extract was stirred in the cold for 30 minutes and centrifuged at 15,000 x g for 15 minutes at 3° C. The supernatant (fraction I, Table I) was recovered and diluted 2-fold by addition of ice cold buffer containing 50 mM Tris-HCl, pH 7.5, 2 mM EDTA and 2 mM DTT. One-tenth volume of a 25% streptomycin sulfate solution was added and the extract was stirred in the cold for 30 minutes followed by centrifugation at 15,000 x for 15 minutes at 3° C.

Solid ammonium sulfate was added to the crude supernatant over a period of 30 minutes to achieve 40% of saturation at 0° C. Stirring was continued for another 30 minutes to achieve 60% of saturation at 0° C. Stirring was continued for another 30 minutes and the precipitate was collected by centrifugation and discarded. The supernatant was recovered and additional solid ammonium sulfate was added over a period of 30 minutes and the precipitate, which contained the aI4α endonuclease activity, was collected by centrifugation at 15,000 x g for 15 minutes at 3° C. and resuspended in buffer containing 10 mM potassium phosphate, pH 7.5, 45% glycerol and 2 mM EDTA and stored at −20° C. (fraction Ia in Table I).

Figure 4:
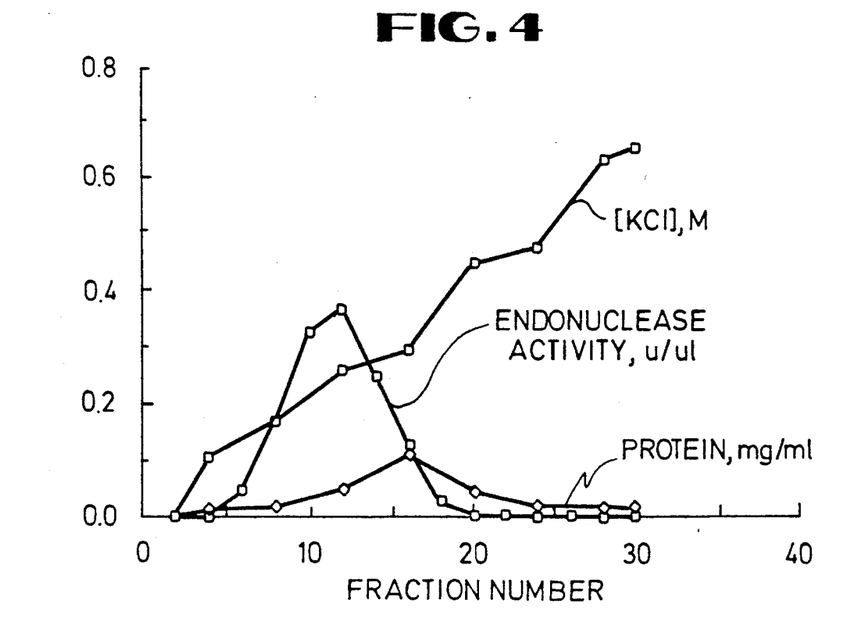
FIG. 4: Purification of the restriction endonuclease by affigel heparin chromatography.
Figure 5:
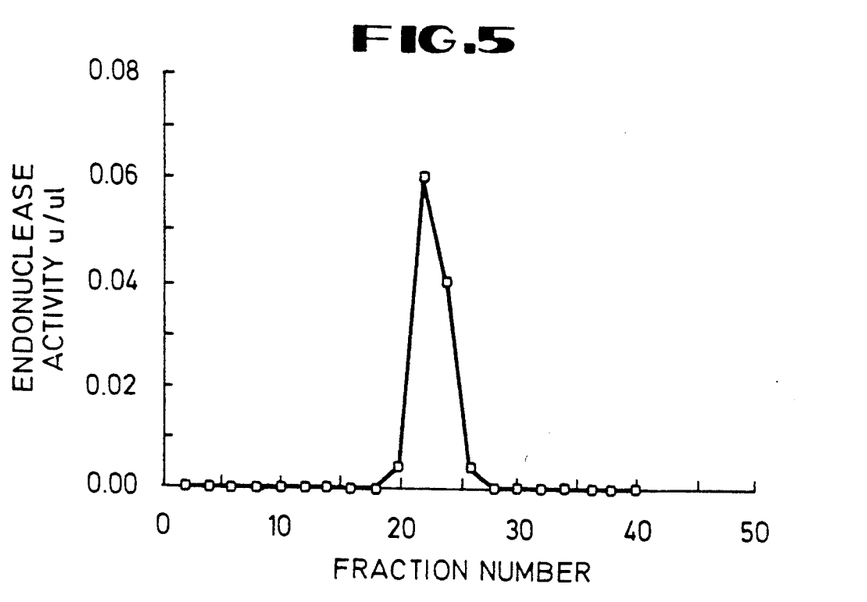
FIG. 5: Purification of the restriction endonuclease by gel filtration.
Figure 6:
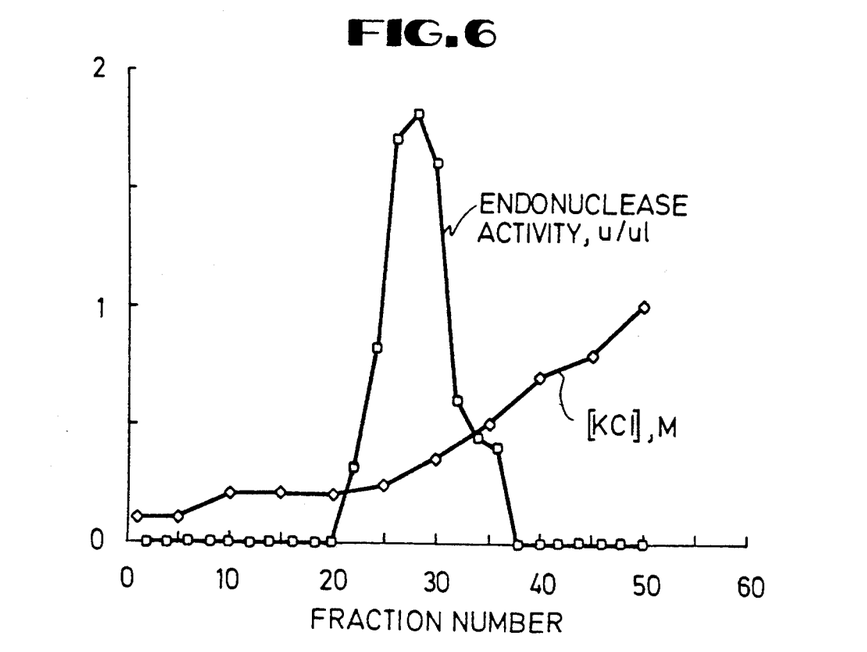
FIG. 6: Purification of the restriction endonuclease by DNA affinity chromatography.

The next step in the purification was to subject fraction Ia (Table I) to phosphocellulose chromatography. The details of the procedure are described in FIG. 3. Fractions showing endonuclease activity were pooled (fraction II in Table I) and dialyzed against Buffer A until an ionic equivalent of 50 mM KCl was reached. This dialyzed fraction was then applied to an Affigel Heparin column (FIG. 4). The active fractions from this procedure were pooled to form Fraction III (Table I). This pooled fraction was then applied to a Sephacryl HS200 column (FIG. 5). The active fractions obtained from gel filtration were pooled to form Fraction IV (Table I). This fraction was applied to a DNA affinity column (FIG. 6). The pooled active fractions (V, Table I) were mixed with an equal volume of 50 mM potassium phosphate, pH7.5, 80% glycerol and 3 mM EDTA and stored at −20° C.

EXAMPLE 5

Analysis of mtDNA

Mitochondrial DNA was prepared by the procedure of Bingham and Nagley (1983). Restriction enzyme digestions were performed as recommended by the enzyme supplier (Bethesda Research Laboratories). Fragments were separated on 1% agarose or 6% polyacrylamide gels and transferred by the well-known method of Southern (1975) or electrophoretically to Hybond-N membranes (Amersham). Hybond-N membranes were prehybridized in 6x SSC containing 10x Denhardt's, 0.5% SDS, and 0.5 mg/ml of calf thymus DNA at 65° C. Oligonucleotides were end-labeled with T4 polynucleotide kinase and allowed to hybridize to membranes for 2 hr at 42° C. Blots were washed three times for 15 min each at 50° C. in 6x SSC. Other probes, generated by the multiprime DNA labeling system (Amersham), were hybridized to membranes overnight at 42° C. Blots were washed twice at 42° C. for 15 min each in 2x SSC, containing 0.1% SDS, and twice for 15 min each in 0.2x SSC, containing 0.1% SDS. All filters were exposed to Kodak XAR-5 X-ray film.

EXAMPLE 6

Extract Preparation and Endonuclease Assay

Galactose-grown cells were harvested at late logarithmic phase, and a mitochondrial fraction was isolated as described by Hudspeth et al. (1980). All further manipulations were done at 4° C. Mitochondria were resuspended in a solution containing 0.6M sorbitol, 25 mM Tris-HCl (pH 7.5), 25 mM EDTA, and 30% Percoll and were further purified by banding in self-forming Percoll gradients obtained by centrifuging the resuspended mitochondria at 15,000 x g for 20 min. The mitochondrial band was isolated and diluted with 10 vol of a solution containing 0.5M NH$_4$Cl and 25 mM Tris-HCl(pH 7.5) and centrifuged at 15,000 x g to pellet the mitochondria. Mitochondria were lysed in a solution containing 50 mM Tris (pH 7.5), 100 mM NH$_4$Cl, 10 mM MgCl$_2$, 2 mM DTT, and 1% NP40. The extract was clarified at 15,000 x g, and the supernatant was used for endonuclease assays. Protein concentration was determined by the BCA protein assay (Pierce Chemical Company).

For the cleavage experiment described in FIG. 8, the substrates pDR1 and pJW1 were linearized with EcoR1 and the overhangs filled in with [α-$^{32}$P]dATP and dTTP using the Klenow fragment. Unincorporated nucleotides were eliminated on a spin column and the DNA was phenol extracted, ethanol precipitated, and resuspended in a solution containing 10 mM Tris (pH 7.5) and 1 mM EDTA. Reactions were performed with 10 ng of substrate in a 25 μl reaction. Reaction conditions for this study were 25 mM Tris(pH 7.5), 25 mM MgCl$_2$, 200 mM NH$_4$Cl, and 2 mM DTT at 30° C. Reactions were allowed to proceed for 5 min and were stopped with 2.5 μl of a solution containing 50 mM Tris (pH 7.5), 100 mM EDTA, 2% SDS, 15% Ficoll, and 1% bromophenol blue. The reaction products were separated on a 1% agarose gel and visualized by autoradiography.

EXAMPLE 7

Mapping of the Cleavage and Recognition Sites

Using a modification of the Sequenase ® (United States Biochemical Corporation) sequencing strategy, the cleavage site was mapped by generating double-stranded substrates from single-stranded templates (phages RS18 and RS19) bearing the cleavage site. Two nanograms of the universal sequencing primer was annealed to 1 μg of each template in a 20 μl Sequenase ® labeling reaction. The reaction was extended with 1 mM dNTPs to generate the "end-labeled" substrate. One-fifth of that material was cleaved with PZ27 extract as described above. An aliquot (1/50) was separated alongside a sequencing ladder generated from the rest of the labeling mixture and separated on 5% polyacrylamide gels. To determine the boundaries of the recognition site, cleavage reactions were performed on the sequencing ladders themselves (FIGS. 9 and 10).

While the invention is susceptible to various modifications and alternative forms, specific embodiments thereof have been shown by way of example in the drawings and have been described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

REFERENCES

The references listed below are incorporated herein by reference to the extent that they supplement, explain, provide a background for or teach methodology, techniques and/or compositions employed herein.

1. Bingham, C. G. and Nagley, P. A petite mitochondrial DNA segment arising in exceptionally high frequency in a mit-mutant of *Saccharomyces cerevisiae*, Biochem. Biophys. Acta., 740:88 (1983).
2. Bonitz, S. E., et al. Assembly of the mitochondrial membrane system. Structure and nucleotide sequence of the gene coding for submit I of yeast cytochrome oxidase, J. Biol. Chem. 255:11927–11941.
3. Butow, R. A. Non-reciprocal exchanges in the yeast mitochondrial genome, Trends Genet. 1:81 (1985).
4. Butow, R. A., et al. The unusual var1 gene of yeast mitochondrial DNA, Science 228:1496 (1985).
5. Colleaux, L., et al. Universal code equivalent of a yeast mitochondrial intron reading frame is expressed -continued into *E. coli* as a specific double strand endonuclease, Cell 44:521 (1986).
6. Delahodde, A., et al. Site specific DNA endonuclease and RNA maturase activities of two homologous intron-encoded proteins from yeast mitochondria, Cell 56:431 (1989).
7. Dujardin, G., et al. Single base substitution in an intron of oxidase gene compensates splicing defects of the cytochrome b gene, Nature 298:628 (1982).
8. Hanson, D. K., et al. Evidence for translated intervening sequences in the mitochondial genome of *Saccharomyces cerevisiae*, J. Biol. Chem. 257:3218 (1982).
9. Herbert, C. J., et al., The NAM2 protein from *Saccharomyces cerevisiae* and *S. douglassi*, are mitochondrial leucyl tRNA synthetases and are involved in mRNA splicing, EMBO J 7:473 (1988).
10. Hudspeth, M., et al. Rapid purification of yeast mitochondrial DNA in high yield. Biochem. Biophys. Acta. 610:221 (1980).
11. Jacquier, A., Dujon, B. An intron-encoded protein isactive in a gene conversion process that spreads an intron into a mitochondrial gene, Cell 41:383 (1985).
12. Kotylak, Z., et al. Intron encoded proteins inmitochondrial: key elements of gene expression and genomic evolution. In Achievements and Perspectives of Mitochondrial Research, v. II, Biogenesis, Quagliaiello, E. C. et al. (eds.), Elsevier Science Publishers B.V., Amsterdam, p. 1 (1985).
13. Lewin, B. Genes III, Chap. 4, Chap. 18, Wiley and Sons, N.Y. (1987).
14. Perlman, P. S., et al. Mosaic genes in yeast mitochondria. In Gene Structure and Expression, Dean, D. B. et al. (eds.) The Ohio State University Press, Columbus, Ohio, p. 1 (1980).
15. Ralph, D. Evolution of cytoplasmic genones. Ph.D. Thesis. The Ohio State University, Columbus, Ohio (1986).
16. Wenzlau, J. M., et al. A latent intron-encoded maturase is also an endonuclease needed for intron mobility, Cell 56:421 (1989).
17. deZamaroczy, M., Bernardi, G. The primary structure of the mitochondrial genome of *Saccharomyces cerevisiae* - A review, Gene 47:155 (1986).
18. Zassenhaus, H. P. Genetic and biochemical characterization of mitochondrial mutants in the var1 region of *Saccharomyces cerevisiae*, Ph.D. Thesis, The Ohio State University (1979).

What is claimed is:

1. An endonuclease protein encoded in the fourth intron of yeast cytochrome oxidase having an apparent molecular weight of about 29,000 daltons as determined by SDS-PAGE, and which is capable of cleaving double-stranded DNA at a site identified as follows:

$$\downarrow$$
D N G G B C A B B C W G A R G T D D
H N C C V G T V V G W C T Y C A H H.
$$\uparrow$$

2. The endonuclease protein of claim 1, further defined as a mitochondrial-derived enzyme.
3. The endonuclease protein of claim 2, further defined as a mitochondrial enzyme derived from yeast.
4. The endonuclease protein of claim 3, further defined as a *Saccharomyces cerevisiae*-derived enzyme.
5. The endonuclease of claim 1, further defined as having a biological activity of up to about 100 units/mg protein.
6. The endonuclease of claim 5 further defined as having a biological activity of up to about 34,000 units/mg after phosphocellulose chromatography.
7. The endonuclease of claim 6 further defined as having a biological activity of up to about 50,000 units/mg after heparin chromatography.
8. The endonuclease of claim 7 further defined as having a biological activity of up to about 200,000 units/mg after gel filtration.
9. The endonuclease of claim 8 further defined as having a biological activity of up to about 500,000 units/mg after DNA affinity chromatography.
10. The endonuclease of claim 1 wherein the endonuclease is translated from a fusion between the upstream exons of the mitochondrial cytochrome oxidase subunit I gene (cox1) of yeast and the open reading frame (ORF) within the 4th intron (aI4α) of the cox1 gene.
11. The endonuclease of claim 1 wherein the enzyme is capable of cleaving recipient DNA molecules near the site of yeast mitochondrial cox1 intron (aI4α) insertion.
12. The endonuclease of claim 1 which is also capable of acting as a maturase under certain conditions, said conditions comprising the coincidence of a point mutation in the intron reading frame, the mim-2 mutation or the presence of the nuclear NAM2 gene.
13. A method for preparing an endonuclease having the capability of cleaving double stranded DNA, comprising the steps:
  (a) culturing yeast that are incapable of splicing the aI4α intron of the cox1 gene;
  (b) preparing a mitochondrial extract from the yeast;
  (c) fractionating the extract; and
  (d) selecting a fraction or fractions which comprises an endonuolease as defined by claim 1.
14. The method in claim 13 wherein the yeast comprises the WA12/PZ27 strain of *Saccharomyces cerevisiae*.
15. The method in claim 13 wherein the yeast comprises a strain incapable of expressing the bI4 maturase activity of the cytochrome b gene (cob) in an appropriate culture media.
16. A method of cleaving DNA comprising the steps of:
  (a) preparing an enzyme as defined by claim 1; and
  (b) incubating the enzyme with DNA so as to effectuate the endonucleolytic cleaving of the DNA.

* * * * *